United States Patent [19]

Schwartz

[11] 4,028,808
[45] June 14, 1977

[54] CROZAT APPLIANCE AND METHOD OF MANUFACTURING SAME

[76] Inventor: Robert Schwartz, 1271 Westfield Ave., Rahway, N.J. 07065

[22] Filed: May 17, 1974

[21] Appl. No.: 470,732

[52] U.S. Cl. .............................................. 32/14 E
[51] Int. Cl.² ........................................... A61C 7/00
[58] Field of Search ......................................... 32/14

[56] References Cited

UNITED STATES PATENTS 3,162,948  12/1964  Gerber .............................. 32/14 E

FOREIGN PATENTS OR APPLICATIONS 981,973  6/1951  France

OTHER PUBLICATIONS

Space Maintainers, p. 13, Crozat, Apr. 1, 1968.

Primary Examiner—Robert Peshock
Attorney, Agent, or Firm—J. E. Luecke

[57] ABSTRACT

Improved Crozat appliances useful in the treatment of maxillary and/or mandibular dental malocclusion are provided by the present invention. The improved appliance consists of clasp means that have anterior and interior sections and which are adapted to engage the outer periphery of a molar or premolar on each side of the dental arch. The clasp means are interconnected with a body wire which has an essentially flat spiral spring formed in a segment thereof and adapted to exert a spring extension force against the clasp means. The improved Crozat appliances are prepared by (a) sectioning a maxillary or mandibular dental cast longitudinally to form lateral cast halves; (b) reconstructuring the section cast by locating the cast halves laterally of each other such that the cross-arch width distance between anatomical features of the cast halves correspond substantially to the cross-arch width distance of an ideal arch structure; and (c) constructing a Crozat appliance in substantial conformance to the reconstructed cast by forming clasp means to engage at least a portion of the outer periphery of a molar or premolar on each side of the dental arch of the reconstructed cast and interconnecting the clasp means with a body wire which has an essentially flat spiral spring formed in a segment thereof.

5 Claims, 4 Drawing Figures

CROZAT APPLIANCE AND METHOD OF MANUFACTURING SAME

BACKGROUND OF THE INVENTION

1. Field of the Invention

This invention is directed to an improved Crozat appliance useful in the treatment of maxillary and/or mandibular dental malocclusion and to a technique for forming the improved Crozat appliance. More particularly, the invention is concerned with a preprogrammed Crozat appliance that permits efficient tooth movement without constant need for adjustment and to a technique for its manufacture.

2. Description of the Prior Art

The use of Crozat appliances in maxillofacial orthopedics is well established. In the first stage of Crozat therapy, the patient is normally fitted with maxillary and/or mandibular Crozat appliances that cause, by steady application of a small force, the movement of certain anterior and posterior teeth. The typical Crozat appliance consists of clasp members which are adapted to engage one or more posterior teeth on each side of the dental arch. The clasp members are interconnected with a single body wire which is crimped in a special manner to provide a spring extension force which serves to cause movement of selected teeth. The object of the use of the wire appliances is to bring the patient's dentition into conformance with a pre-established ideal arch structure. To accomplish this end, the practitioner must frequently readjust the conventional Crozat appliance to accommodate changes accomplished with the use of the appliance until the specifications of the desired ideal arch formation are reached in the patient's arch form. Making the necessary periodic adjustments is a time-consuming and difficult task requiring the practitioner to make constant measurements and very exacting adjustments of the Crozat appliance.

SUMMARY OF THE INVENTION

In accordance with the present invention, improved Crozat appliances are provided which are pregrogrammed to bring the dentition under treatment into conformance with an ideal arch structure without frequent adjustment. The improved Crozat appliance comprises clasp means having anterior and interior portions that are adapted to engage at least a portion of the outer periphery of a molar or premolar on each side of the dental arch (mandibular arch or maxillary arch) and a body wire, preferably a metallic body wire, that is connected to the interior portions of each of the clasp means, the body wire having an essentially flat spiral spring formed in a segment thereof which is adapted to exert a spring extension force against the clasp means.

The improved Crozat appliance is prepared using a special fabrication technique. In brief, the technique involves (a) sectioning a maxillary or mandibular cast substantially along its longitudinal axis to form lateral cast halves; (b) reconstructing the cast halves by locating and positioning the cast halves laterally of each other such that the cross-arch width distance between anatomical features of the cast halves correspond substantially to the cross-arch width distance of an ideal arch structure; and (c) constructing a Crozat appliance in substantial conformance to the reconstructed cast prepared pursuant to steps (a) and (b) and comprising forming clasp means having anterior and interior portions to engage at least a portion of the outer periphery of a molar or premolar on each side of the dental arch of the reconstructed cast and interconnecting the interior portions of each of the clasps with a metallic body wire, the body wire having an essentially flat spiral spring formed in a segment thereof and adapted to exert a spring extension force against the clasp means.

BRIEF DESCRIPTION OF THE DRAWINGS

The invention will be more readily understood by reference to the accompanying drawings in which:

As shown in FIGS. 2 and 4, the Crozat appliance of the present invention comprises clasp means 10 that have interior and anterior portions 11 and 12. The clasp means are adapted to engage at least a portion of the outer periphery of either a molar or premolar on each side of the dental arch. In FIG. 2, the clasp means are shown in contact with the mandibular first molar on each side of the arch. In FIG. 4, the clasp means engage the maxillary 6-year molars (first molars). The interior portions of each of the clasp means 10 are interconnected with a metallic body wire 13. Preferably, the body wire is fabricated from a one-piece, fine gauge wire such as 21 gauge No. 7 gold wire. In a segment of the body wire, preferably the central segment, is formed a flat spiral spring that is adapted to exert a spring extension force against the clasp means 10. One or more such spiral spring 14 may be formed into the body wire; however, generally one spiral spring is sufficient to generate the very small forces required to force the patient's dentition into the desired ideal arch form structure. Generally, the spiral spring 14 is made up of a single loop as excessive spring volume can interfere with the soft tissues of the palatal and lingual areas of the mouth when the appliance is in place. Various other elements may be added to the basic Crozat appliance structure. For example, distal extensions used to move the 12-year molars and recurved springs to contact and/or move cuspids may be soldered or otherwise added to the basic structure. These additional elements are added typically during the later stages of Crozat therapy.

Figure 1:
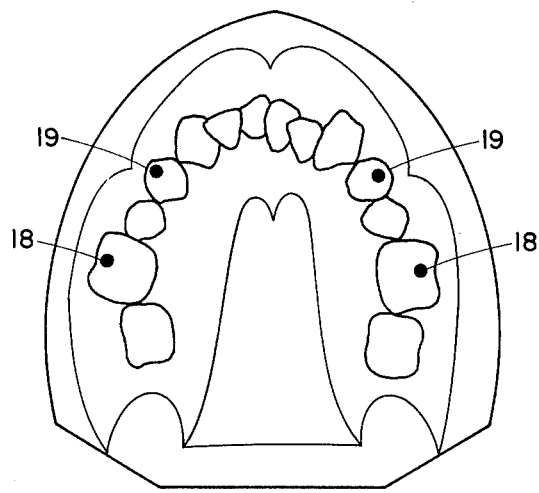
FIG. 1 depicts a maloccluded mandibular arch structure.
Figure 2:
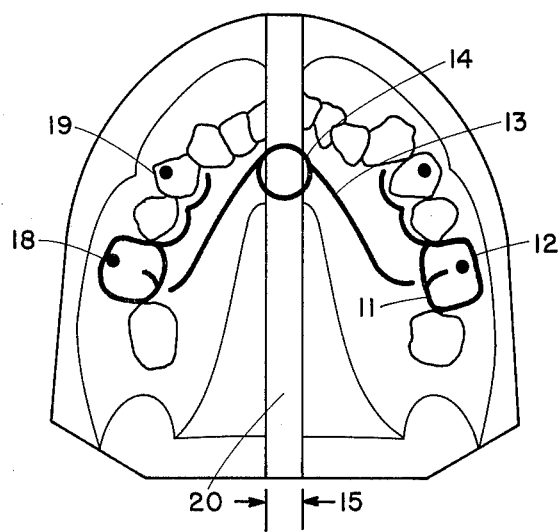
FIG. 2 represents the sectioned and reconstructed FIG. 1 arch structure having located thereon an improved mandibular Crozat appliance of the present invention.
Figure 3:
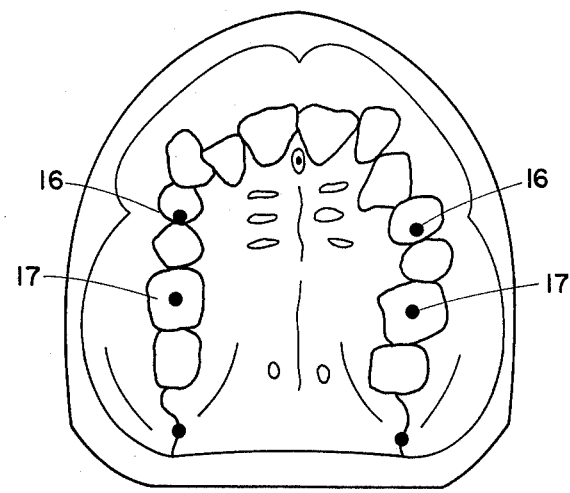
FIG. 3 depicts a maloccluded maxillary arch structure.
Figure 4:
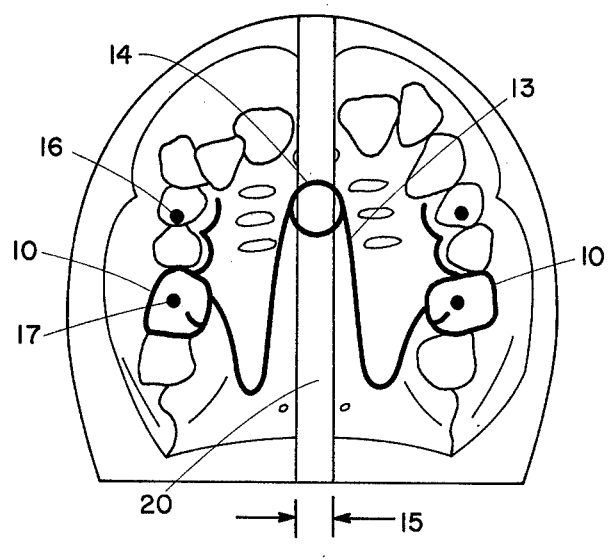
FIG. 4 is a representation of the FIG. 3 arch structure that has been previously sectioned along its longitudinal axis and reconstructed and containing thereon an improved maxillary Crozat appliance of the present invention.

The Crozat appliance described above is adapted to fit the desired future arch form of the patient, that is, it is preprogrammed to produce a desired arch form result. The improved Crozat appliance is prepared using restructured casts of the patient's dental anatomy. In preparing the appliance, maxillary and/or mandibular casts (FIGS. 1 and 3) prepared from impressions of the patient's maxillary and/or mandibular arch structure are sectioned substantially along their longitudinal axis to form lateral cast halves. Preferably, the maxillary cast is sectioned, as depicted in FIG. 4, along the maxillary raphe of the cast. The mandibular cast, as depicted in FIG. 2, is desirably sectioned along a line connecting the midpoint between the genial tubercles and the midpoint between the mylohyoid ridges at the first molar area. It is desirable that the bases of the maxillary and/or mandibular casts used in preparing the appliance be essentially parallel to Camper's Plane. Such casts can be prepared utilizing the apparatus and techniques described in U.S. Pat. No. 3,465,443 the disclosures of which are herein incorporated by reference.

The sectioned casts are then reconstructured by locating the cast halves of the maxillary and/or madibular arch structure laterally of each other such that the cross-arch width distance between anatomical features of the cast halves correspond substantially to the cross-arch width distance of an ideal arch structure. In practice, the cast halves are separated by a distance 15 sufficient to increase the cross-arch distance between anatomical features found on each of the cast halves to a point where such distances correspond to the distance of an ideal arch structure.

In the first stage of classic Crozat therapy, the practitioner attempts to increase the cross-arch width distance between the ligual cusps of the upper first premolars 16 and the cross-arch width distance between the central fossae of the upper 6-year molars 17 into conformance with the cross-arch distances of a predetermined ideal arch structure (generally in conformance with Pont's Index for the desired arch form). Similarly, in the case of the mandibular arch, the practitioner endeavors to increase the cross-arch width distance between the mid-buccal cusp of the lower-year molars 18 and distance between the distal pits of the lower first premolars 19 until such distances are in conformance with the distances found on an ideal arch structure (generally in conformance with the W and P Indices for the desired arch form). Hence, distance 15 of the separated cast is determined by the extent to which the cross-arch width distance of an ideal arch structure exceeds the cross-arch distances of the patient's actual arch structure.

After distance 15 has been established, the cast halves are fixed in position relative to each other and used as a basis for the manufacture of the improved Crozat appliance of the present invention. Typically, plaster 20 is used to lute the two cast halves together in the desired fixed position.

The reconstructed cast is thereafter used as a basis for constructing a Crozat appliance. Specifically, clasp means are formed on the molar or premolar on each side of the dental arch of the reconstructed cast and are interconnected with a body wire, preferably a one piece body wire, that has an essentially flat spiral spring formed in a segment thereof. The appliance thus formed on the reconstructed cast, when placed on the existing dentition of the patient, is preprogrammed to force the patient's dentition into conformance with an ideal arch structure.

What is claimed is:

1. A method of fabricating a Crozat appliance useful in the treatment of dental malocclusion which comprises:
  a. longitudinally sectioning a dental cast to form lateral cast halves;
  b. restructuring said cast halves by locating said cast halves laterally of each other such that the cross-arch width distance between anatomical features of said cast halves correspond substantially to the cross-arch width distance of an ideal arch structure; and
  c. constructing a Crozat appliance in substantial conformance to said reconstructed cast comprising forming clasp means having anterior and interior portions to engage at least a portion of the outer periphery of a molar or premolar on each side of the arch of said reconstructed cast and interconnecting the interior portions of said clasp means with a body wire, said body wire having an essentially flat spiral spring formed in a segment thereof and adapted to exert a spring extension force against said clasp means.

2. The method of claim 1 wherein the base of said longitudinally sectioned cast is essentially parallel to Camper's Plane.

3. The method of claim 1 wherein said body wire is a one-piece metallic wire.

4. The method of claim 1 wherein said spiral spring is formed in a central segment of said body wire.

5. The method of claim 3 wherein said spiral spring is formed in a central segment of said body wire.

* * * * *